United States Patent
Damaj (10) Patent No.: US 11,696,899 B2
(45) Date of Patent: Jul. 11, 2023

(54) ORAL COMPOSITIONS COMPRISING CINNAMALDEHYDE AND USES THEREOF

(71) Applicant: INNOVUS PHARMACEUTICALS, INC., San Diego, CA (US)

(72) Inventor: Bassam Damaj, San Diego, CA (US)

(73) Assignee: INNOVUS PHARMACEUTICALS, INC., San Diego, CA (US)

( * ) Notice: Subject to any disclaimer, the term of this patent is extended or adjusted under 35 U.S.C. 154(b) by 82 days.

(21) Appl. No.: 17/136,932

(22) Filed: Dec. 29, 2020

(65) Prior Publication Data

US 2022/0202740 A1    Jun. 30, 2022

(51) Int. Cl.

| | | |
|---|---|---|
| *A61K 31/11* | (2006.01) | |
| *A61K 9/00* | (2006.01) | |
| *A61K 9/48* | (2006.01) | |
| *A61P 25/02* | (2006.01) | |
| *A61P 3/10* | (2006.01) | |
| *A61K 36/88* | (2006.01) | |
| *A61K 31/675* | (2006.01) | |
| *A61K 36/481* | (2006.01) | |
| *A61K 36/258* | (2006.01) | |
| *A61K 36/67* | (2006.01) | |
| *A61K 36/54* | (2006.01) | |

(52) U.S. Cl.
CPC ............ *A61K 31/11* (2013.01); *A61K 9/0053* (2013.01); *A61K 9/4858* (2013.01); *A61K 9/4866* (2013.01); *A61K 9/4875* (2013.01); *A61K 31/675* (2013.01); *A61K 36/258* (2013.01); *A61K 36/481* (2013.01); *A61K 36/54* (2013.01); *A61K 36/67* (2013.01); *A61K 36/88* (2013.01); *A61P 3/10* (2018.01); *A61P 25/02* (2018.01)

(58) Field of Classification Search
None
See application file for complete search history.

(56) References Cited

U.S. PATENT DOCUMENTS

| | | | | |
|---|---|---|---|---|
| 2009/0175848 A1* | 7/2009 | Lee | ......................... | A61K 31/26 |
| | | | | 435/375 |
| 2018/0344680 A1* | 12/2018 | Zhang | .................. | A61K 31/192 |

OTHER PUBLICATIONS

May (F1000 Medicine Reports (2009), vol. I, No. 76, 4 pages).*
"Trexar® Product Webpage," AYTU BioScience, Inc., Aug. 2020, 3 pages [retrieved online from: web.archive.org/web/20200803210641/https:/mytrexar.com/].
"What is Trexar®," AYTU BioScience, Inc., Aug. 2020, 2 pages [retrieved online from: web.archive.org/web/20200803201821/https:/mytrexar.com/what-is-trexar/].
"Science Behind Trexar®," AYTU BioScience, Inc., Sep. 2020, 3 pages [retrieved online from: web.archive.org/web/20200926075002/https:/mytrexar.com/science-behind-trexar/].
"Trexar® FAQ," AYTU BioScience, Inc., Sep. 2020, 4 pages [retrieved online from: web.archive.org/web/20200926082743/https:/mytrexar.com/faq/].
"How should I take Trexar®," AYTU BioSceince, Inc., Oct. 2020, 2 pages [retrieved online from: web.archive.org/web/20201028091726/https:/mytrexar.com/how-should-i-take-trexar/].
Balakumar et al. "The multifaceted therapeutic potential of benfotiamine," Pharmacological Research, Jun. 2010, vol. 61, No. 6, pp. 482-288.
Bandell et al. "Noxious cold ion channel TRPA1 is activated by pungent compounds and bradykinin," Neuron, Mar. 2004, vol. 41, No. 6, pp. 849-857.

* cited by examiner

*Primary Examiner* — Susan Hoffman
(74) *Attorney, Agent, or Firm* — Sheridan Ross P.C.

(57) ABSTRACT

Oral compositions comprising cinnamaldehyde, and methods or improving circulation and improving circulation by administering such compositions, are described. Methods and uses are describe that include the administration of an effective amount of the oral compositions to improve circulation and increasing nerve sensitization, while also resulting in improved balance, and reduced pain, numbness, and/or tingling in the hands and feet, as well as reduced restlessness, fatigue, and tiredness of the legs.

19 Claims, 10 Drawing Sheets

ORAL COMPOSITIONS COMPRISING CINNAMALDEHYDE AND USES THEREOF

BACKGROUND

Field

The present disclosure generally relates to compositions and methods for improving circulation and supporting nerve health. More specifically, the present disclosure generally relates to oral cinnamaldehyde formulations, and methods of using such formulations for increasing nerve sensitization.

Description of the Related Art

The circulatory system is responsible for delivering blood, nutrients, and oxygen throughout the body. Many people suffer the effects of poor circulation, which may include acute or chronic numbness in the extremities, coldness in the extremities, and swollen ankles, feet, wrists, hands or fingers. Poor circulation may be attributable to underlying medical conditions such as atherosclerosis and diabetes. Additional causes of poor circulation may the result of other factors such as the effect of certain medications, lack of exercise, smoking, and/or obesity.

TRPA1 is an ion channel located on the plasma membrane of many human and animal cells. This ion channel is recognized as a sensor for environmental irritants giving rise to somatosensory modalities, such as pain, cold, and/or itching. TRPA1 is considered a pain target. Moreover, studies show that TRPA1 functions as a cold sensor in mammals. Thus, proper function of TRPA1 may support nerve sensation, particularly with respect to proper cold sensation.

Diabetic neuropathies are a family of nerve disorders caused by diabetes. People with diabetes can, over the course of the disease, develop nerve damage throughout the body, and nerve problems can occur in every organ system, including the digestive tract, heart, and sex organs. About 60 to 70 percent of people with diabetes have some form of neuropathy, and the neuropathy can cause loss of sensitivity in the feet and hands. Increasing sensitivity of the remaining nerves of neuropathy patients may result in increased sensation, ease the symptoms of neuropathy, and greatly improve a person's quality of life.

Based on the above, there exists a need for methods of improving and maintaining circulatory and nerve health.

SUMMARY

Methods are provided for increasing nerve sensation without increasing pain, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not increasing pain in the subject. Method are also provided for increasing nerve sensation without increasing numbness, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not increasing numbness in the subject. Methods are also provided for increasing nerve sensation without increasing swelling, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not increasing swelling in the subject. Methods are also provided for increasing nerve sensation without increasing tingling, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not increasing tingling in the subject. Method are also provided for increasing nerve sensation without increasing fatigue, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not increasing fatigue in the subject. Methods are also provided for increasing nerve sensation without decreasing mobility, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) not decreasing mobility in the subject. Method are also provided for increasing nerve sensation while improving balance, the method comprising the steps of: (i) identifying a subject in need of increased nerve sensation; (ii) administering a therapeutically effective amount of an oral formulation comprising cinnamaldehyde to the subject; and thereby (iii) increasing nerve sensation in the subject, while (iv) improving balance in the subject.

The disclosed method may involve the oral administration of compositions that further comprises at least one of the members of the group consisting of: cinnamon bark extract; garlic extract (bulb) extract; benfotiamine; astralagus root extract; and *Ginseng panax* root. The disclosed methods may involve the oral administration of compositions that further comprising at least one pharmaceutically acceptable excipient. These optional excipients may be selected from the group consisting of: rice flour, magnesium stearate, maltodextrin, microcrystalline cellulose, and combinations thereof. The oral composition may be formulated as a capsule. The capsule may comprises from about 125 mg to 175 mg, and preferably comprises about 150 mg, of cinnamon bark extract. The capsule may comprises about 125 mg to 175 mg, and preferably comprises about 150 mg, or garlic bulb extract. The capsule may comprise about 75 mg to 125 mg, and preferably comprises about 100 mg, of benfotiamine. The capsule may comprise about 7.5 mg to 12.5 mg, and preferably comprises about 10 mg, of an astralagus root extract/*Ginseng panax* root blend.

The oral composition may be administered one, two, three, or four times a day. Each dosage may involve the administration of two capsules. The composition may be administered over a period of at least one month, or at least two months.

The subject being treated may experience one or more conditions selected from poor circulation, diabetes, reduced nerve sensation, neuropathy, numbness in the extremities, tingling in the extremities, cold hands and feet, poor mobility, poor balance, swelling in lower extremities, fatigue, stinging in arms and legs, and combinations thereof. The subject may be identified by analyzing the results of a questionnaire.

DETAILED DESCRIPTION OF THE PREFERRED EMBODIMENT

In some embodiments, an oral composition is provided comprising cinnamaldehyde, which is a component of cinnamon bark extract. The composition may also comprise at least one of the following: garlic extract (bulb), benfotiamine, astralagus root extract, *Ginseng panax* root, and bioperine. In some embodiments, the oral composition may further include one or more excipients including, but not limited to, rice flour, magnesium stearate, maltodextrin, and microcrystalline cellulose. In some embodiments, the oral composition may be formulated as a capsule.

In some embodiments, the compositions provided herein include cinnamon bark extract. Cinnamon bark extract includes cinnamaldehyde and is also rich in tannins, a class of phenolic compounds linked to health benefits due to their antioxidant properties. In some embodiments, the cinnamon bark extract contains approximately 0.75%, 1%, or 1.25% polyphenols. In some embodiments, the amount of cinnamon bark extract in the oral composition may be, for example, at least about 20 wt. %, at least about 25 wt. %, at least about 30 wt. %, at least about 33 wt. %, at least about 35 wt. %, at least about 36 wt. %, at least about 37 wt. %, at least about 38 wt. %, at least about 39 wt. %, at least about 40 wt. %, at least about 45% wt. %, or within a range defined by any two of the aforementioned concentrations. For example, in some embodiments, the amount of cinnamon bark extract present in the oral composition will range from, for example, approximately 30 wt. % to approximately 37 wt. %, from approximately 31 wt. % to approximately 36 wt. %, from approximately 32 wt. % to approximately 35 wt. %, or from approximately 33 wt. % to approximately 34 wt. %.

In some embodiments, the compositions provided herein include garlic extract (bulb). Garlic extract (bulb) has been considered to be beneficial for health and contains compounds with antioxidant, anti-infective, anti-hypertensive, and cholesterol-lowering properties. Without being bout to any particular theory, regular ingestion of garlic extract may improve circulation and be preventative for atherosclerosis and cardiovascular diseases. In some embodiments, the garlic extract contains approximately 0.75%, 1%, or 1.25% allicin. In some embodiments, the amount of garlic extract (bulb) in the oral composition may be, for example, at least about 20 wt. %, at least about 25 wt. %, at least about 30 wt. %, at least about 33 wt. %, at least about 35 wt. %, at least about 36 wt. %, at least about 37 wt. %, at least about 38 wt. %, at least about 39 wt. %, at least about 40 wt. %, at least about 45 wt. %, or within a range defined by any two of the aforementioned concentrations. For example, in some embodiments, the amount of garlic extract (bulb) present in the oral composition will range from, for example, approximately 30 wt. % to approximately 37 wt. %, from approximately 31 wt. % to approximately 36 wt. %, from approximately 32 wt. % to approximately 35 wt. %, or from approximately 33 wt. % to approximately 34 wt. %.

In some embodiments, the compositions provided herein include benfotiamine. Benfotiamine is metabolized in the body to thiamine. Because benfotiamine is absorbed by the body better than thiamine, benfotiamine can increase thiamine levels in the body. Without being bound by any particular theory, benfotiamine may aid in the treatment of a number of disorders, including neuropathy, anxiety, and alcoholism. In some embodiments, the amount of benfotiamine in the oral composition may be, for example, at least about 15 wt. %, at least about 17 wt. %, at least about 18 wt. %, at least about 19 wt. %, at least about 20 wt. %, or at least about 21 wt. %, at least about 22 wt. %, at least about 23 wt. %, or at least about 24 wt. %, at least about 25 wt. %, or within a range defined by any two of the aforementioned concentrations. For example, in some embodiments, the amount of benfotiamine present in the oral composition will range from, for example, approximately 16 wt. % to approximately 26 wt. %, from approximately 18 wt. % to approximately 24 wt. %, or from approximately 20 wt. % to approximately 22 wt. %.

In some embodiments, the compositions provided herein include a blend of astralagus root extract and *Ginseng panax* root. Astralagus has many purported health benefits, including immune-boosting and anti-inflammatory effects. It is also thought to have preventative effects against heart disease, diabetes, kidney disease, and other conditions. *Panax ginseng* is a plant that grows in Korea, northeastern China, and far eastern Siberia. *Panax ginseng* is thought to contain many active substances that may have beneficial effects on blood glucose levels and cognitive performance. The blend of astralagus root and *ginseng panax* root may be supplied as a blend including, but not limited to AstraGin®. In some embodiments, the amount of astralagus root extract and *Ginseng panax* root blend in the oral composition may be, at least about 1.5 wt. %, at least about 1.7 wt. %, at least about 1.8 wt. %, at least about 1.9 wt. %, at least about 2.0 wt. %, or at least about 2.1 wt. %, at least about 2.2 wt. %, at least about 2.3 wt. %, at least about 2.4 wt. %, or at least about 2.5 wt. % or within a range defined by any two of the aforementioned concentrations. For example, in some embodiments, the amount of the blend of astralagus root and *Ginseng panax* root present in the oral composition will range from, for example, approximately 1.6 wt. % to approximately 2.6 wt. %, from approximately 1.8 wt. % to approximately 2.4 wt. %, or from approximately 2.0 wt. % to approximately 2.2 wt. %. Accordingly, in some embodiments, the amount of the of each of astralagus root and *Ginseng panax* root present in the oral composition will range from, for example, approximately 0.8 wt. % to approximately 1.3 wt. %, from approximately 0.9 wt. % to approximately 1.2 wt. %, or from approximately 1.0 wt. % to approximately 1.1 wt. %.

In some embodiments, the compositions provided herein include black pepper extract. Black pepper extract is a supplement extracted from the fruit of the black pepper and is thought to increase the bioavailability of certain nutritional compounds. Black pepper extract is commercially available as BioPerine®. In some embodiments, the amount of black pepper extract in the oral composition may be, for example, at least about 0.5 wt. %, at least about 0.7 wt. %, at least about 0.8 wt. %, at least about 0.9 wt. %, at least about 1.0 wt. %, or at least about 1.1 wt. %, at least about 1.2 wt. %, at least about 1.3 wt. %, at least about 1.4 wt. %, or at least about 1.5 wt. % or within a range defined by any two of the aforementioned concentrations. For example, in some embodiments, the amount of black pepper extract present in the oral composition will range from, for example, approximately 0.7 wt. % to approximately 1.6 wt. %, from approximately 0.9 wt. % to approximately 1.4 wt. %, or from approximately 1.0 wt. % to approximately 1.2 wt. %.

In some embodiments, a method is provided for increasing nerve sensation without increasing pain. The method comprises the steps of: (i) identifying a subject in need of increased nerve sensation; (ii) administering a therapeutically effective amount of an oral formulation disclosed herein to the subject; and thereby (iii) increasing nerve sensation in the subject, while (iv) not increasing pain in the subject.

In other embodiments, a method is provided for increasing nerve sensation without increasing numbness. The method may comprise the steps of: (i) identifying a subject in need of increased nerve sensation; (ii) administering a therapeutically effective amount of an oral formulation disclosed herein to the subject; and thereby (iii) increasing nerve sensation in the subject, while (iv) not increasing numbness in the subject.

In other embodiments, method is provided for increasing nerve sensation without increasing swelling. The method comprises the steps of: (i) identifying a subject in need of increased nerve sensation; (ii) administering a therapeutically effective amount of an oral formulation disclosed herein to the subject; and thereby (iii) increasing nerve sensation in the subject, while (iv) not increasing swelling in the subject.

In other embodiments, a method is provided for increasing nerve sensation without increasing tingling. The method comprises the steps of: (i) identifying a subject in need of increased nerve sensation; (ii) administering a therapeutically effective amount of an oral formulation disclosed herein to the subject; and thereby (iii) increasing nerve sensation in the subject, while (iv) not increasing tingling in the subject.

In other embodiments, a method is provided for increasing nerve sensation without increasing fatigue. The method comprises the steps of: (i) identifying a subject in need of increased nerve sensation; (ii) administering a therapeutically effective amount of an oral formulation disclosed herein to the subject; and thereby (iii) increasing nerve sensation in the subject, while (iv) not increasing fatigue in the subject.

In some embodiments, a method is provided for increasing nerve sensation without decreasing mobility. The method comprises the steps of: (i) identifying a subject in need of increased nerve sensation; (ii) administering a therapeutically effective amount of an oral formulation disclosed herein to the subject; and thereby (iii) increasing nerve sensation in the subject, while (iv) not decreasing mobility in the subject.

In other embodiments, provided herein is a method of increasing nerve sensation while improving balance, the method comprising the steps of: (i) identifying a subject in need of increased nerve sensation; administering a therapeutically effective amount of an oral formulation disclosed herein to the subject; and thereby (iii) increasing nerve sensation in the subject, while (iv) improving balance in the subject.

In some embodiments, the subject can be identified through the use of a questionnaire. For example, potential subjects are asked to provide responses to questions related to their age, genetic and/or medical histories, present symptoms and severity thereof, current medications. In some embodiments, the subject self-identifies and experiencing one or more conditions selected from poor circulation, diabetes, reduced nerve sensation, neuropathy, numbness in the extremities, tingling in the extremities, cold hands and feet, poor mobility, poor balance, swelling in lower extremities, fatigue, stinging in arms and legs, and combinations thereof. The subject completes the questionnaire before administering the oral composition, optionally during a course of administration of the oral composition, and after a course of administration of the oral composition. The results of the questionnaire indicate that the administration of the oral composition leads to an improved assessment of nerve sensation without the subject experiencing one or more of the following adverse conditions: numbness in the extremities, tingling in the extremities, cold hands and cold feet, poor mobility, poor balance, swelling in lower extremities (e.g., legs, ankles, feet, and/or toes), swelling in upper extremities (e.g., arms, wrists, hand, and/or fingers), fatigue, stinging in arms and legs, and combinations thereof.

In some embodiments, the oral composition is administered once per day, two times per day, three times per day, or four times per day, preferably two times per day. In some embodiments, the compounds will be administered for a period of continuous therapy, for example for one day, for two days, for three days, for a week, for two weeks, for one month, for two months, for three months, for four months, for five months, for six months, seven month, for eight months, for nine months, for ten months, for eleven months, for twelve months, for eighteen months, for two years, for three years, for four years, or for five or more years.

In some embodiments, the oral compositions disclosed herein may formulated into an oral dosage form. In some embodiments, the oral dosage form may be a capsule. In some embodiments, the capsule may comprise from about 100 mg to about 200 mg, or from about 125 mg to about 175 mg, or about 150 mg cinnamon bark extract. In some embodiments, the capsule may comprise from about 100 mg to 200 mg, or from about 125 mg to about 175 mg, or about 150 mg garlic extract (bulb). In some embodiments, the capsule may comprise from about 50 mg to about 150 mg, or from about 75 mg to about 125 mg, or about 100 mg benfotiamine. In some embodiments, the capsule may comprise from about 5.0 mg to about 15.0 mg, or from about 7.5 mg to about 12.5 mg, or about 10.0 mg astralagus root extract/*Ginseng panax* root blend. In some embodiments, the capsule may comprise from about 1.0 mg to about 10.0 mg, or from about 2.5 mg to about 7.5 mg, or about 5.0 mg black pepper extract. In some embodiments, the compositions disclosed herein may further comprise one or more pharmaceutically acceptable excipients or carriers.

In some embodiments, the dose administered to the subject may be one, two, three, four, or more capsules. In some embodiments each dose may comprise two capsules. In some embodiments, four capsules are administered to the subject per day.

The terms "pharmaceutically acceptable carrier" and "pharmaceutically acceptable excipient," as used herein, include any and all pharmaceutically-acceptable solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

The term "excipient," as used herein, refers to an inert or relatively inert substance that is added to a pharmaceutical composition to impart certain properties to the composition including, without limitation, improved or desired bulk, consistency, stability, binding ability, lubrication, disintegrating ability, etc. A "diluent" is a type of excipient.

In some embodiments, the oral composition disclosed herein may comprise an excipient selected from rice flour, magnesium stearate, maltodextrin, microcrystalline cellulose, and combinations thereof.

EXAMPLES

Example 1

Materials used in preparing the oral cinnamaldehyde compositions described herein may be made by known methods or are commercially available. It is also possible to make use of variants which are themselves known to those of ordinary skill in this art, but are not mentioned in greater detail. The skilled artisan given the literature and this disclosure is well equipped to prepare the formulations of the instant application.

Representative oral compositions are shown in Table 1 below, with the amounts for "broad", "intermediate" and "preferred" ranges.

TABLE 1

Representative Oral Compositions

| Component | Broad Ranges (mg) | Intermediate Ranges (mg) | Preferred Amounts (mg) |
|---|---|---|---|
| Active Ingredients | | | |
| Cinnamon bark extract (1% polyphenols) | 100-200 | 125-175 | 150 |
| Garlic extract (Bulb) (1% allicin) | 100-200 | 125-175 | 150 |
| Benfotiamine | 50-150 | 75-125 | 100 |
| Astralagus Root Extract and Ginseng Panax Root (as a blend) | 5-15 | 7.5-12.5 | 10 |
| Bioperine (Black Pepper Extract) | 1-10 | 2.5-7.5 | 5.0 |
| Optional Excipients | | | |
| Rice flour | 0-25 | 12.5-20 | 17.5 |
| Magnesium Stearate | 0-20 | 12.5-20 | 17.5 |
| Maltodextrin | 0-20 | 5-12.5 | 12.5 |
| Microcrystalline Cellulose | 0-20 | 5-12.5 | 12.5 |
| Total | 415-500 | 450-480 | 475 |

Example 2

Subjects over the age of 18, in need of therapy for increasing nerve sensation, were identified through a multipart questionnaire. Subjects provided information age, weight, height, and indicated whether they suffered from reduced nerve sensation and underlying medical conditions including diabetes and neuropathy. Subjects were also asked about whether they suffered from poor circulation and discomfort from poor circulations such as numbness and tingling in extremities, cold hands and feet, swelling in lower extremities, fatigue, restless legs, mobility, poor mobility, restless legs, trouble sleeping, and stinging in arms and legs, and to rate the discomfort on a scale of 1 to 10, with 1 being no bother and 10 being severe discomfort.

Subjects were administered two capsules, each containing the preferred formulation of Example 1, twice a day for four months. Subjects were provided with a questionnaire to self-assess their symptoms, and their severity, as compared to their initial assessments.

Figure 1:
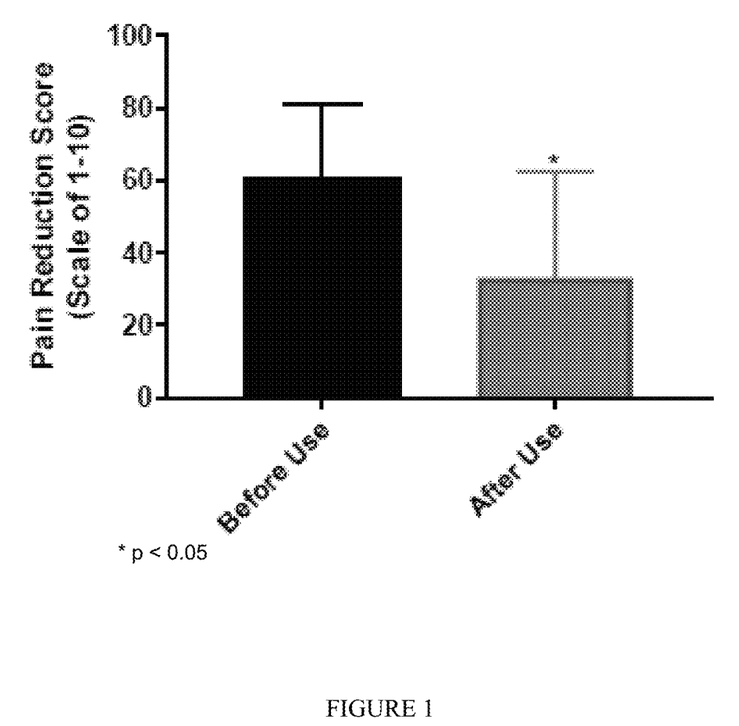
FIG. 1 graphically depicts the results of surveys of ten subjects regarding the effect of a formulation disclosed herein (the preferred formulation of Example 1) on pain reduction in the hands and feet of human subjects.
Figure 2:
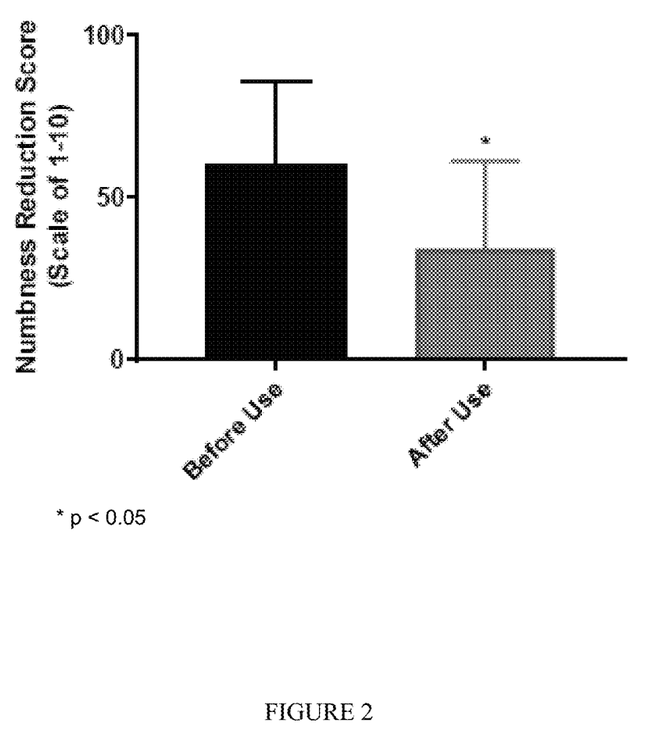
FIG. 2 graphically depicts the results of surveys of ten subjects regarding the effect of s formulation disclosed herein (the preferred formulation of Example 1) on numbness reduction in the hands and feet of human subjects.
Figure 3:
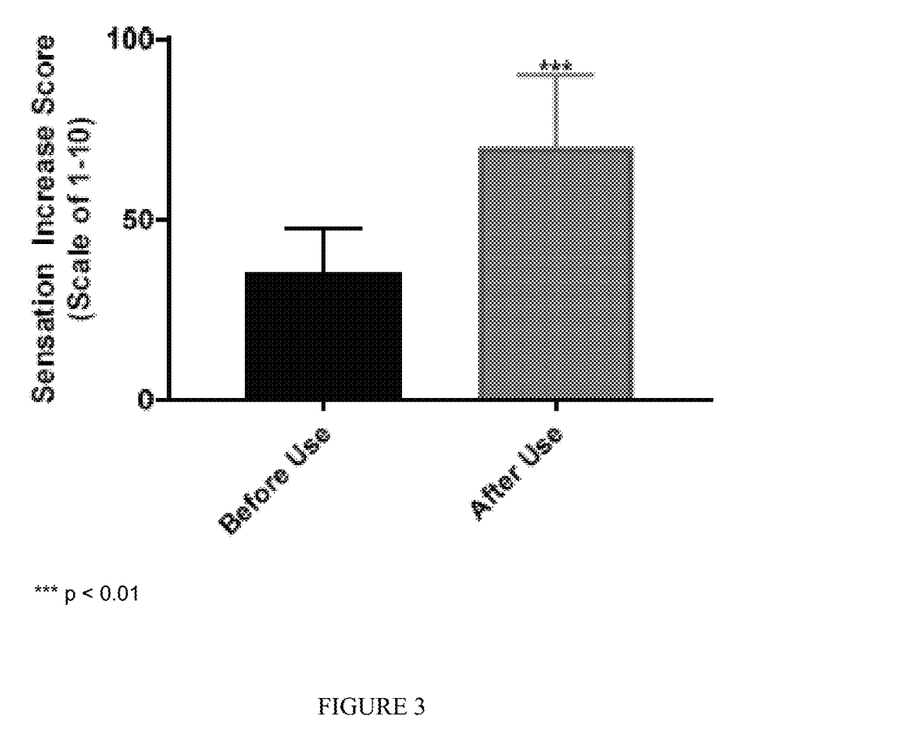
FIG. 3 graphically depicts the results of surveys of ten subjects regarding the effect of a formulation disclosed herein (the preferred formulation of Example 1) on sensation increase in the hands and feet of human subjects.
Figure 4:
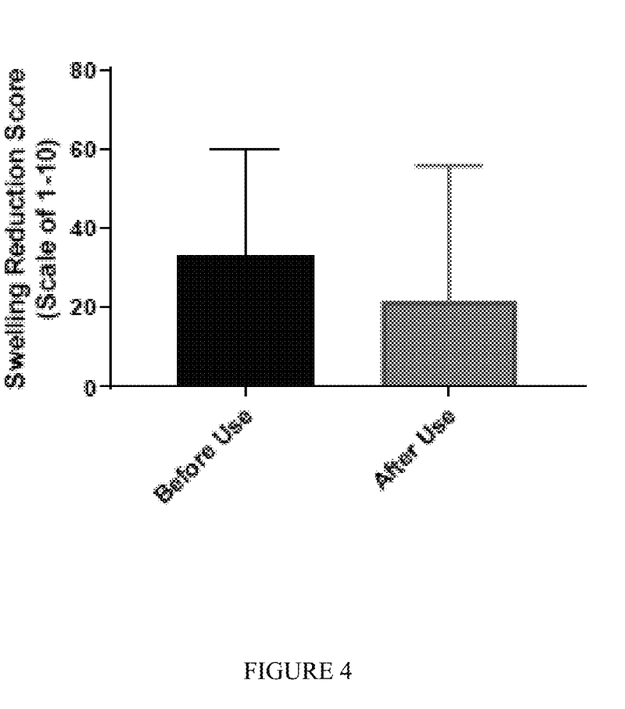
FIG. 4 graphically depicts the results of surveys of six subjects regarding the effect of a formulation disclosed herein (the preferred formulation of Example 1) on swelling reduction in the hands and feet of human subjects.
Figure 5:
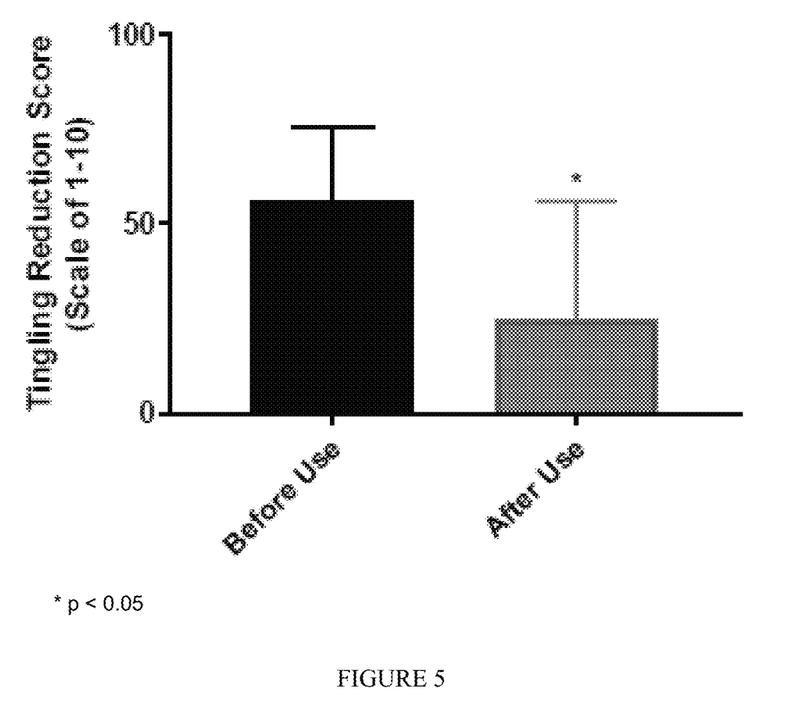
FIG. 5 graphically depicts the results of surveys of ten subjects regarding the effect of a formulation disclosed herein (the preferred formulation of Example 1) on tingling reduction in the hands and feet of human subjects.
Figure 6:
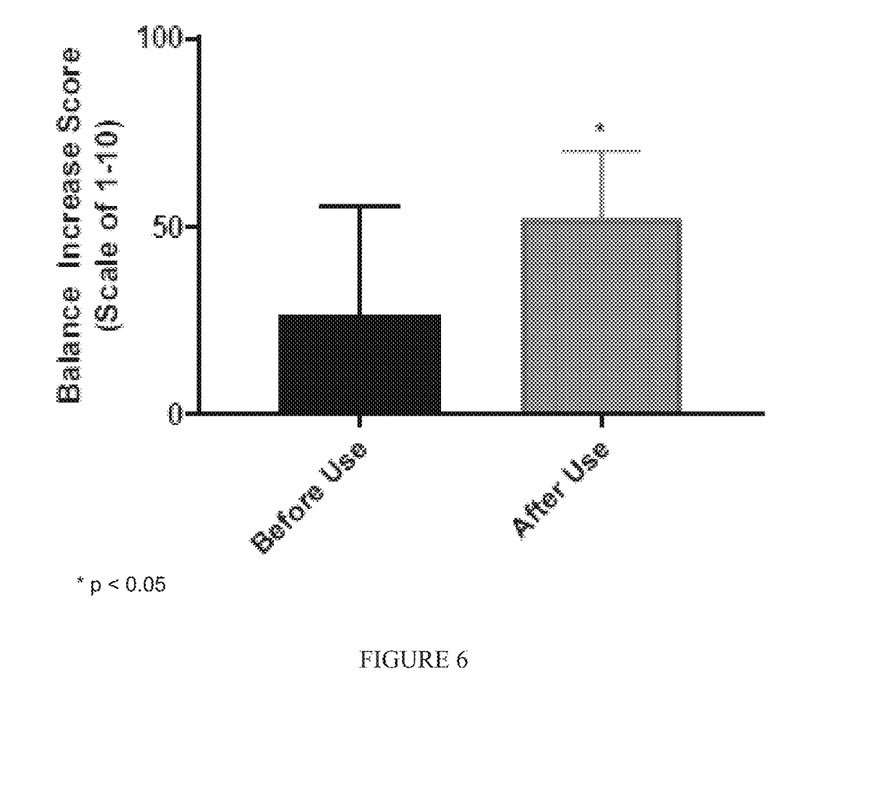
FIG. 6 graphically depicts the results of surveys of eight subjects regarding the effect of a formulation disclosed herein (the preferred formulation of Example 1) on balance increase for human subjects.
Figure 7:
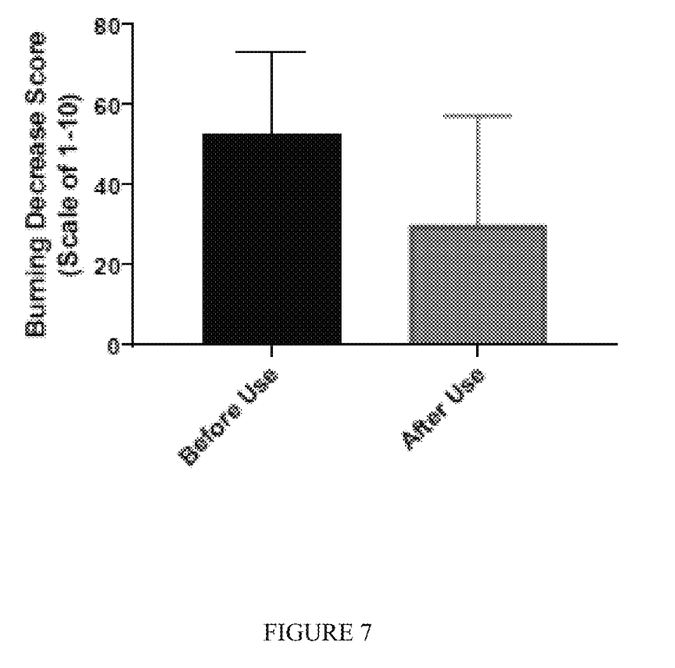
FIG. 7 graphically depicts the results of surveys of eight subjects regarding the effect of a formulation disclosed herein (the preferred formulation of Example 1) on burning sensation reduction in the hands and feet of human subjects.
Figure 8:
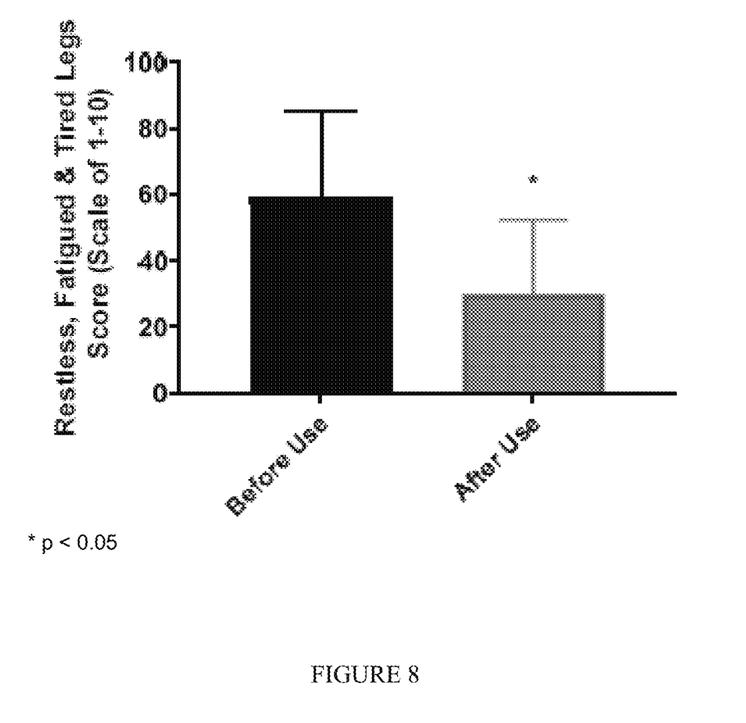
FIG. 8 graphically depicts the results of surveys of nine subjects regarding the effect of a formulation disclosed herein (the preferred formulation of Example 1) on the reduction in the occurrence of restless, fatigued, and tired legs of human subjects.
Figure 9:
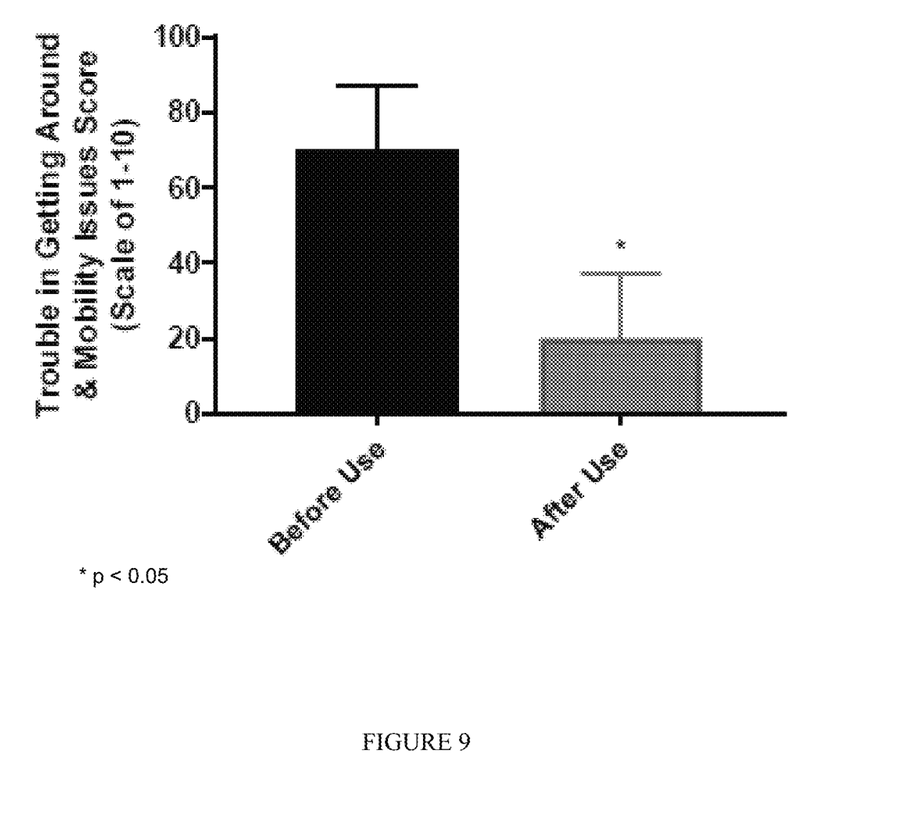
FIG. 9 graphically depicts the results of surveys of three subjects regarding the effect of a formulation disclosed herein (the preferred formulation of Example 1) on the decrease in trouble in getting around and mobility issues score of human subjects.
Figure 10:
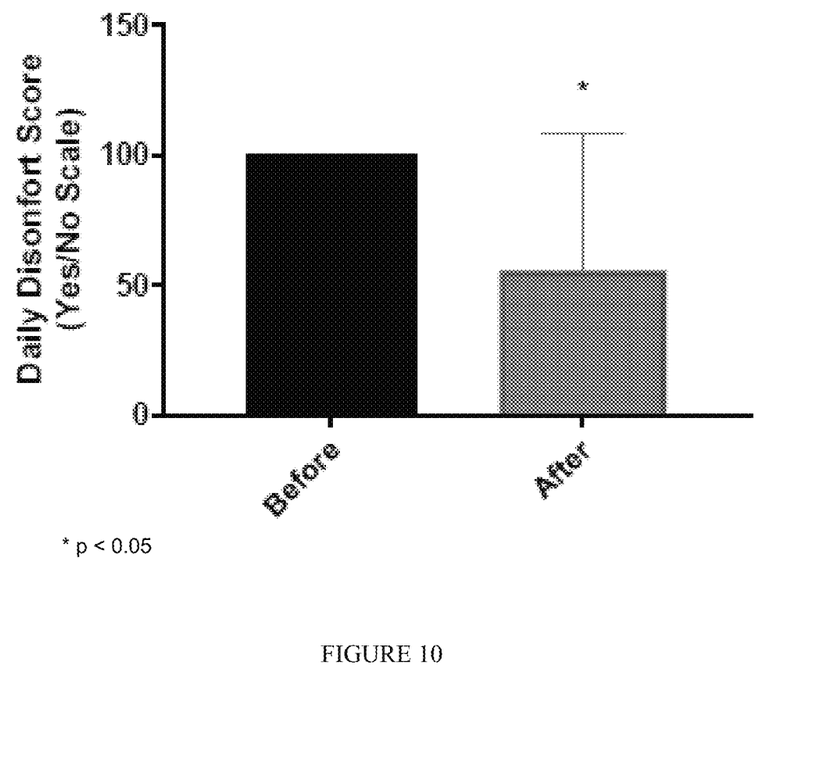
FIG. 10 graphically depicts the results of surveys of nine subjects regarding the effect of a formulation disclosed herein (the preferred formulation of Example 1) on the decrease in daily discomfort score of human subjects.

Administration of the preferred formulation of Example 1 resulted in improvements in various patient conditions. In particular, based on survey results from ten subjects, administration of the preferred formulation of Example 1 resulted in a statistically significant (p=0.234) reduction in pain in the hands and feet of approximately 54 percent (see FIG. 1), a statistically significant (p=0.0416) reduction in numbness in the hands and feet of approximately 56 percent (see FIG. 2), and a statistically significant (p=0.0002) increase in sensation in the hands and feet of approximately 50 percent (see FIG. 3). Based on survey results from ten subjects, administration of the preferred formulation of Example 1 resulted in a statistically significant (p=0.0155) reduction in tingling in the hands and feet of approximately 45 percent (see FIG. 5). Based on survey results from eight subjects, administration of the preferred formulation of Example 1 resulted in a statistically significant (p=0.0223) improvement in balance of approximately 50 percent (see FIG. 6). Based on survey results from nine subjects, administration of the preferred formulation of Example 1 resulted in a statistically significant (p=0.0241) reduction in restless, fatigued, and tired legs of approximately 50 percent (see FIG. 8). Based on survey results from three subjects, administration of the preferred formulation of Example 1 resulted in a statistically significant (p=0.0241) decrease in trouble getting around and mobility issues of approximately 71 percent (see FIG. 9). Based on survey results from nine subjects, administration of the preferred formulation of Example 1 resulted in a statistically significant (p=0.0223) decrease in daily discomfort of approximately 56 percent (see FIG. 10). Based on survey results from six subjects, administration of the preferred formulation of Example 1 also showed a reduction in swelling of the hands and feet (see FIG. 4) and a reduction of burning sensations in the hands and feet (see FIG. 7), although these data do not show a statistically significant reductions in these effects. Accordingly, the preferred formulation of Example 1 demonstrates significant, discrete beneficial effects when administered to subjects.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of increasing nerve sensation comprising administering a therapeutically effective amount of an oral formulation comprising cinnamaldehyde, cinnamon bark extract, garlic bulb extract, benfotiamine, astragalus root extract, and *Panax ginseng* root to a subject in need thereof, wherein:
the oral formulation increases nerve sensation in the subject and causes an effect in the subject selected from: not increasing pain, not increasing numbness, not increasing tingling, not increasing fatigue, not decreasing mobility, improving balance, and combinations thereof.

2. The method of claim 1, wherein the oral formulation further comprises at least one pharmaceutically acceptable excipient.

3. The method of claim 2, wherein the excipient is selected from the group consisting of rice flour, magnesium stearate, maltodextrin, microcrystalline cellulose, and combinations thereof.

4. The method of claim 1, wherein the oral formulation is a capsule.

5. The method of claim 4, wherein the capsule comprises about 125 mg to 175 mg cinnamon bark extract.

6. The method of claim 5, wherein the capsule comprises about 150 mg cinnamon bark extract.

7. The method of claim 4, wherein the capsule comprises about 125 mg to 175 mg garlic bulb extract.

8. The method of claim 7, wherein the capsule comprises about 150 mg garlic bulb extract.

9. The method of claim 4, wherein the capsule comprises about 75 mg to 125 mg benfotiamine.

10. The method of claim 9, wherein the capsule comprises about 100 mg benfotiamine.

11. The method of claim 4, wherein the capsule comprises about 7.5 mg to 12.5 mg of a combination of astragalus root extract and *Panax ginseng* root.

12. The method of claim 11, wherein the capsule comprises about 10.0 mg of the combination.

13. The method of claim 1, wherein the oral formulation is administered one, two, three, or four times a day.

14. The method of claim 13, wherein the oral formulation is administered as two capsules.

15. The method of claim 1, wherein the oral formulation is administered for at least one month.

16. The method of claim 1, wherein the oral formulation is administered for at least two months.

17. The method of claim 1, wherein the subject has a condition selected from the group consisting of poor circulation, diabetes, reduced nerve sensation, neuropathy, numbness in the extremities, tingling in the extremities, cold hands and feet, poor mobility, poor balance, swelling in lower extremities, fatigue, stinging in arms and legs, and combinations thereof.

18. The method of claim 1, wherein the subject is identified by analyzing the results of a questionnaire.

19. The method of claim 1, wherein the oral formulation further comprises black pepper extract.

\* \* \* \* \*